(12) United States Patent
Kobneck

(10) Patent No.: US 11,929,154 B2
(45) Date of Patent: Mar. 12, 2024

(54) MOBILE DEVICE WITH SELECTIVE DISABLEMENT OF FEATURES

(71) Applicant: Novum Patent Holdco, LLC, Loveland, CO (US)

(72) Inventor: Michael A. Kobneck, Broomfield, CO (US)

(*) Notice: Subject to any disclaimer, the term of this patent is extended or adjusted under 35 U.S.C. 154(b) by 0 days.

(21) Appl. No.: 18/053,943

(22) Filed: Nov. 9, 2022

(65) Prior Publication Data

US 2023/0121002 A1 Apr. 20, 2023

Related U.S. Application Data

(63) Continuation of application No. 17/372,681, filed on Jul. 12, 2021, now Pat. No. 11,527,309, which is a continuation of application No. 16/730,468, filed on Dec. 30, 2019, now Pat. No. 11,094,401, which is a continuation of application No. 15/147,507, filed on Feb. 5, 2016, now abandoned.

(51) Int. Cl.
| | |
|---|---|
| G06Q 20/00 | (2012.01) |
| G16H 10/20 | (2018.01) |
| G16H 30/40 | (2018.01) |
| G16H 40/67 | (2018.01) |

(52) U.S. Cl.
CPC ............ *G16H 10/20* (2018.01); *G16H 30/40* (2018.01); *G16H 40/67* (2018.01); *G06Q 2220/00* (2013.01)

(58) Field of Classification Search
CPC ........ G16H 10/20; G16H 30/40; G16H 40/67; G06Q 2220/00
USPC .......................... 705/16, 21, 59; 380/44, 262
See application file for complete search history.

(56) References Cited

U.S. PATENT DOCUMENTS 8,587,600 B1 * 11/2013 Tischler ................. G09G 5/363
345/557

* cited by examiner

*Primary Examiner* — Dante Ravetti
(74) *Attorney, Agent, or Firm* — Russell Krajec; Krajec Patent Offices, LLC

(57) ABSTRACT

Patient identification is transmitted to a health care provider prior to the patient arriving at the health care provider. The patient identification may be a driver's license, health insurance card, or other identification, and may be used to pre-register the patient. The transmission may include other information, such as health status, purpose of visit, intended procedures, symptoms, or other information. The transmission may be made via a device, such as a cellular telephone, where the information may be encrypted and transmitted using a secure mechanism. The system may be used by ambulance personnel, paramedics, or other emergency responders to notify a hospital, for example, of an inbound patient, as well as by patients prior to an appointment. The system may also be used by clinicians or other health care providers to prepare for emergent or non-emergent patients prior to arrival.

9 Claims, 7 Drawing Sheets

100 PATIENT IDENTIFICATION TRANSMISSION SYSTEM

MOBILE DEVICE WITH SELECTIVE DISABLEMENT OF FEATURES

CROSS REFERENCE TO RELATED APPLICATIONS

This application claims priority to and benefit of U.S. patent application Ser. No. 17/372,681 entitled "Medical Registration System" filed 12 Jul. 2021, U.S. patent application Ser. No. 16/730,468 entitled "Medical Registration System" filed 30 Dec. 2019, and U.S. patent application Ser. No. 15/017,507 entitled "Medical Registration System" filed 5 Feb. 2016.

BACKGROUND

Prior to medical treatment, a patient generally registers and performs other administrative functions prior to being treated at a hospital, doctor's office, or other service provider. The registration allows a service provider to gather background information, access the patient's records, establish payment or insurance procedures, or other administrative functions.

SUMMARY

Patient identification is transmitted to a health care provider prior to the patient arriving at the health care provider. The patient identification may be a driver's license, health insurance card, or other identification, and may be used to pre-register the patient. The transmission may include other information, such as health status, purpose of visit, intended procedures, symptoms, or other information. The transmission may be made via a device, such as a cellular telephone, where the information may be encrypted and transmitted using a secure mechanism. The system may be used by ambulance personnel, paramedics, or other emergency responders to notify a hospital, for example, of an inbound patient. The system may also be used by clinicians or other health care providers to prepare for emergent or non-emergent patients prior to arrival.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Patient Registration System

Figure 1:
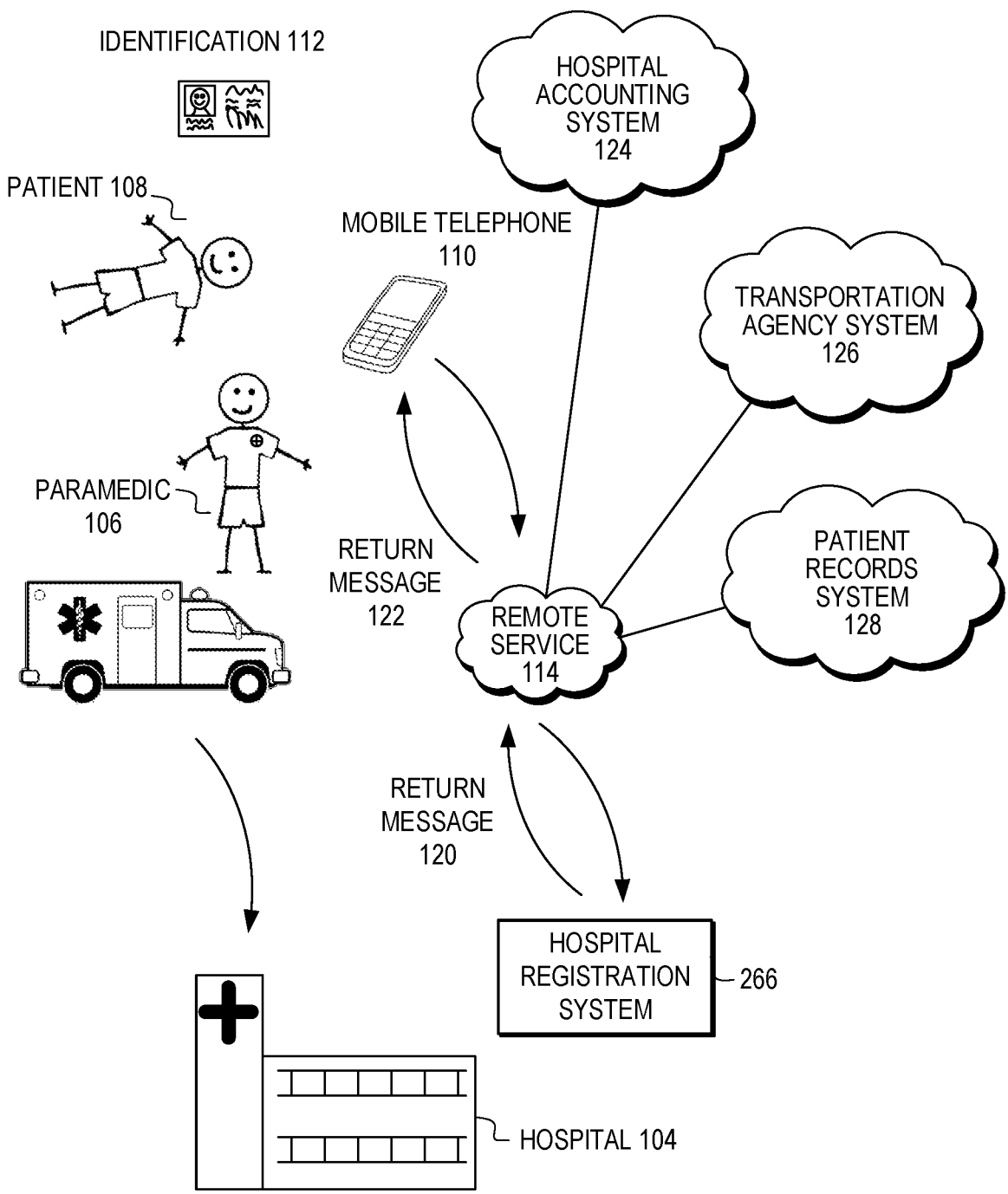
FIG. 1 is a diagram illustration of an embodiment showing a patient identification system.

Patient identification may be transmitted to a health care provider prior to the patient arriving at the provider. The information may include identification information, such as a driver's license or other identification. The information may be used to check in or register a patient prior to the patient's arrival at a health care facility. The information may be considered Personally Identifiable Information (PII) and may be protected data under various legislation, such as Health Insurance Portability and Accountability Act (HIPAA) in the United States, which may have regulations about data that may be considered private and protected.

One use scenario is the transportation of a patient by an ambulance to a hospital. A paramedic may take a picture of the patient's driver's license, insurance card, or other identifying information, and may transmit the picture to the hospital. The hospital may be able to register the patient prior to arrival, saving valuable time for the patient to receive medical assistance. In many cases, such a pre-registration system may minimize the administrative tasks of the ambulance crew while at the hospital, resulting in the ambulance crew being ready to take another call.

Such a scenario may reduce administrative time in an emergent situation. For example, a pre-registration performed by an ambulance crew may allow a hospital's emergency department to access the patient's medical records prior to arrival, as well as to eliminate any administrative overhead when the patient arrives and before being seen by a medical provider.

Another use scenario is for a patient to transmit identifying documents prior to visiting a health care provider, such as a doctor's office, therapist, hospital, or other provider. In a non-emergent situation, a patient may use a system to transmit their identifying information to the provider when scheduling an appointment or some time prior to arriving at the provider. The information may be forwarded to an admittance system that may prepare for the patient's arrival. In some cases, the information may be forwarded to a billing and records system to enter the patient's information for billing and health care records purposes. By pre-registering the patient, a health care provider or administrative assistant may have forms or other systems that may be pre-populated for easy data entry.

The system may use secure mechanisms to capture and transmit patient information to the service provider. The secure mechanisms may encrypt the data being transmitted, and in many cases, may not store patient information in a manner that may be easily accessed. In many cases, the patient information may be stored on transmitting device, but may be in an encrypted form.

A cellular telephone or other mobile device may be used to capture and transmit patient information to a healthcare provider. The mobile device may have a camera, keyboard, or other data collection device that may gather information. The information may be encrypted at the point of capture, then securely transmitted to the service provider. The service provider may have authenticated and secure access to the information. In many cases, the information may be transmitted to a cloud or other remote database, and the service provider may be provided with credentials for accessing the data. In some cases, the health care provider may have a device that may access the patient information and may or may not store the information on a local device. Such a system may have an application programming interface (API) or other mechanism by which various other systems, such as patient billing systems and health care records systems, may access the information.

An application executing on a cellular telephone or other mobile device may allow a user to capture patient information, encrypt or otherwise secure the information, and may transmit the information. The application may include features for taking photographs of driver's licenses, health insurance information, or other documents, as well as to enter data about the patient's condition, any services rendered prior to arrival at the service provider, and other information. In some cases, the application may capture pictures from an accident scene, pictures of a patient's wounds, or other documentation. Such an application may be provided to a patient's mobile device or to a service provider's mobile device, such as a paramedic, fire fighter, police officer, emergency responder, or other person who may be assisting the patient.

The application may or may not store patient information on the device on which the application executes. The application may transmit the data to a remote service, which may be a device at the service provider, or may be a cloud service that may capture and store the patient information. The cloud service may organize and store the uploaded information and may make the information available to the medical service provider as well as other people and organizations which may have a use for the data.

Various organizations may access the patient data for different uses. In an example described above, a hospital may receive information about inbound patients in an ambulance, and may prepare the patient's registration and plan their care in an emergent situation. However, other organizations may also use the patient data. For example, an ambulance or other transportation service may access the patient information as part of their billing system, insurance companies may access the information as part of claims processing, as well as the patient may access their data. Each person or organization may be permitted to access only a subset of the information. In many cases, an access to the information may be on a need-to-know basis, such that a transportation service that may access the data for billing purposes, may have access to enough information to satisfy a payor of transportation, but may not have access to additional information.

Throughout this specification, like reference numbers signify the same elements throughout the description of the figures.

When elements are referred to as being "connected" or "coupled," the elements can be directly connected or coupled together or one or more intervening elements may also be present. In contrast, when elements are referred to as being "directly connected" or "directly coupled," there are no intervening elements present.

In the specification and claims, references to "a processor" include multiple processors. In some cases, a process that may be performed by "a processor" may be actually performed by multiple processors on the same device or on different devices. For the purposes of this specification and claims, any reference to "a processor" shall include multiple processors, which may be on the same device or different devices, unless expressly specified otherwise.

When elements are referred to as being "connected" or "coupled," the elements can be directly connected or coupled together or one or more intervening elements may also be present. In contrast, when elements are referred to as being "directly connected" or "directly coupled," there are no intervening elements present.

The subject matter may be embodied as devices, systems, methods, and/or computer program products. Accordingly, some or all of the subject matter may be embodied in hardware and/or in software (including firmware, resident software, micro-code, state machines, gate arrays, etc.) Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. By way of example, and not limitation, computer readable media may comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can accessed by an instruction execution system. Note that the computer-usable or computer-readable medium could be paper or another suitable medium upon which the program is printed, as the program can be electronically captured, via, for instance, optical scanning of the paper or other medium, then compiled, interpreted, of otherwise processed in a suitable manner, if necessary, and then stored in a computer memory.

When the subject matter is embodied in the general context of computer-executable instructions, the embodiment may comprise program modules, executed by one or more systems, computers, or other devices. Generally, program modules include routines, programs, objects, components, data structures, etc. that perform particular tasks or implement particular abstract data types. Typically, the functionality of the program modules may be combined or distributed as desired in various embodiments.

FIG. 1 is a diagram illustration of an embodiment 100 showing an example use case for a patient identification transmission system.

Embodiment 100 is merely one illustration of how a patient identification transmission system may be used. In this case, an ambulance 102 may be preparing to transport a patient 108 to a hospital 104. A paramedic 106 may be taking care of the patient 108, and may use a mobile telephone 110 or other device to take a picture of the patient's identification 112. The image of the patient's identification 112 may be transmitted to a cloud service 114, which may further communicate with a hospital registration system 116 where the image may be displayed.

In general, patient identification information may be protected or private information. Patient identification information may be personally identifiable information (PII) that may be regulated by various governments in various manners, and many governments may regulate healthcare related information with additional security precautions. In the United States, for example, patient medical records may be regulated under the Health Insurance Portability and Accountability Act (HIPAA).

Various patient-related information may be considered Protected Health Information (PHI) in some jurisdictions, and typically such information is afforded additional special protection under law. Typical protections include various administrative safeguards that may be in place in order to handle electronic Protected Health Information, such as policies and procedures for the entities handling information, identification of which employees have access to the information and procedures for controlling access to those employees, controls for introduction and disposal of devices which handle such information, access limitations for such devices, intrusion protection for networks and devices on those networks, integrity of the data in the network, authentication of entities that access the information, documentation and control of device settings used to access the network, and other protections.

The scenario of embodiment 100 may have a paramedic 106 or other service provider use a portable device, such as a mobile or cellular telephone to take a picture of a patient's driver's license and transmit the image to a hospital. The image may be the first electronic data about the patient during their treatment and would typically be covered as Protected Health Information.

The mobile telephone 110 used by the paramedic 106 may be configured in several different manners to handle Protected Health Information.

In one configuration, the mobile telephone 110 may be issued and configured by a transportation agency, a hospital or other healthcare provider, or by a third party contracted to provide the device. When the device may be provided and controlled by the transportation agency or the healthcare provider, the device may be configured with various controls that may minimize exposure of patient information. Such controls may include restricting the end user's ability to change settings on the device, removing local storage capabilities, disabling screen capture functions, and other controls. Such a device may further be configured with a remote "self-destruct" feature that may cause the device to wipe itself clean of any data if the device were to be misplaced, lost, or stolen.

Such a configuration may use readily available, consumer-oriented devices, such as cellular telephones, tablet and slate computers, portable cameras, and other devices to gather patient information prior to transporting a patient to a healthcare provider. Many consumer-oriented devices may have various functions that may allow inadvertent or nefarious access to the patient information. Such functions, such as screen capture functions, may be built-in functions that come with a typical consumer-oriented device.

In the example of a screen capture function, a user may be able to create an image of the device's screen, and the image may be stored on the device and manipulated and transmitted like a conventional image. When the screen may be displaying sensitive patient information, an image of the screen from a screen capture function may thereby contain sensitive patient information. By disabling or limiting a screen capture function, a potential security breach may be thwarted.

Local data storage functions may be similarly limited or restricted. When patient information may be locally stored on a mobile device, the data may be vulnerable if other applications on the device may be capable of accessing and manipulating images or other data stored on the device. By restricting various functions on the device for storing, accessing, and manipulating images and other data on the device, another path by which data may be intentionally or unintentionally shared may be closed.

Some systems may have an application that may capture an image or other data and may encrypt the data prior to storing the data on the device. In such an embodiment, any patient data that may be stored on the device may be unintelligible to other applications, so that even if another application were to be able to access the image, the encryption would prevent a user from viewing the image.

User authentication may be enforced prior to capturing patient identification. The authentication may restrict access to the device or the identification capture and transmission application on the device to specific personnel. The authentication mechanism may allow access for a specific individual or for a group of people. In a typical use scenario, paramedics or other first responders who have been trained to use the patient capture system may be given credentials for accessing the device or the application executing on the device to gather and upload patient identification.

In some cases, the user authorization may restrict access to the entire device, while in other cases, separate user authorization may restrict access to an application executing on the device. In the first case, a user may have to enter a password, provide a fingerprint or other biometric identifier, or provide some other credential prior to accessing the device. In the second case, a user may have to enter a second set of credentials to access an application that may collect patient identification and/or for transmitting the patient identification.

Device-level authentication may be used in some systems to authenticate specific devices for access to a remote service. For example, the remote service may be configured with addresses, identifiers, or other indicators of devices through which access may be granted. Any device that may not be in the database of authorized devices may be denied access and may not be able to upload patient data or receive communication from the remote service.

Physical safeguards may restrict the movement of the device used for capturing and transmitting the patient information. In some cases, the device may be physically tethered or rigidly mounted to another object, such as a device that may be mounted within or tethered to an ambulance. For devices that may be portable, the devices may have various features that may actively or passively disable the devices, and in some cases, may actively delete any patient data.

An active disabling mechanism may be any mechanism whereby a remote signal may be sent to the device, and in response, the device may disable itself or may delete sensitive information on the device. Such signals may be sent when the device may be reported missing, for example.

A passive disabling mechanism may be any mechanism whereby a device may automatically disable itself in various situations. In one example, a device may have an operational area in which the device may be authorized to be used. Many devices may have a Global Positioning System receiver or other mechanism to determine the device's location, and when the device is outside of the operational area, the device may become disabled and/or may delete any patient data. In such an example, the movement of the device outside the operational area may be used as an indication that the device may be stolen, misplaced, or otherwise is being used outside of its authorized geographical location.

In another example of a passive disabling mechanism, a device may automatically disable itself when the device has not been used in a period of time. For example, a device that may not have been used in a day, week, or month may be disabled or may have locally stored information deleted. In one version of such a mechanism, a device may have an automatic cleansing system that may delete any locally stored information periodically, such as every hour or every day. Such systems may limit the exposure of unintended or malicious disclosure of information stored on the device.

A cloud or remote service 114 may receive patient information from the mobile telephone 110 and may transmit the information to a hospital 104. The patient information may be displayed on a hospital registration computer system 116.

The remote service 114 may interact with a device such as a mobile telephone 110 by first authenticating a session with the device. The authenticated session may be encrypted and may allow data to be transferred in a secure manner. An authentication mechanism may include authenticating the user of the device, which may be accomplished by receiving user credentials and verifying those credentials. The credentials may be a username and password, a personal identification number, a biometric sensor, or some other set of credentials.

Authentication may include authenticating the device to the remote service. Such an authentication mechanism may involve receiving an identifier, address, or other indicators or credential from the device, then authenticating based on the device's credentials. In some instances, device-level authentication may be sufficient to transmit patient information, while in other instances, both device-level and user-level authentication may be used. In still other instances, user-level authentication may be used without device-level authentication.

In emergency response situations, authentication may become a burden to an emergency responder, who may be focused on dealing with a patient's immediate health issues. A burdensome authentication mechanism may distract the responder, delay their treatment, and maybe cause the responder to skip using the device altogether. In such situations, the authentication mechanism may be limited to a device-level authentication or no authentication at all.

In some use cases, no authentication may be used to transmit patient data. No authentication may be permitted in systems where patient information may be encrypted at the remote device, such as the mobile telephone 110, then transmitted in encrypted form. Use cases may include emergent situations as described above, but also for the general public, such as when a patient wishes to schedule an appointment with a physician or other healthcare provider.

In one version of such a system, the remote service 114 may receive patient information from any device, regardless if the device has previously been used to communicate with the remote service 114. In such a version, the remote service 114 may receive the patient information and may add metadata about the communication, such as the IP or MAC address of the sending device, as well as any other information such as a timestamp and other metadata. Other metadata may include transmission path data, such as an address or identifier for a wireless access point that received the transmission, as well as identifiers for each link in a transmission path. In many cases, such metadata may serve as identification information for a transmission received by the remote service 114 from an unauthenticated user or device.

The physical location of the transmitting device may be included in a message sent to the remote service 114. Physical location information may be determined by a Global Positioning System (GPS) receiver on the transmitting device, as well as by triangulation or other location services. A physical location may be used for identification and authentication uses, as well as to estimate a patient's arrival time at a hospital or treatment center, for example.

The remote service 114 may receive patient information from a transmitting device and may forward the message to a hospital 104 with or without analyzing the contents of the message. In some systems, the remote service 114 may not decrypt the patient information and therefore may not be exposed to privacy issues. In other systems, the remote service 114 may decrypt the patient information and my perform various functions using the patient information.

When the remote service 114 decrypts patient information, the remote service 114 may analyze the patient information, format the patient information, and may transmit the patient information to various systems, including the hospital registration computer system 116, a hospital accounting system 124, a transportation agency system 126, a patient records system 128, or other systems.

In many cases, the patient information may be in the form of an image of an identification document, such as a driver's license, insurance card, or other document. The remote service 114 may perform optical character recognition on the image and may extract various data, such as the person's name, address, date of birth, social security number, insurance plan information, or other information that may be present on the document. Such information may be analyzed and placed into fields of a patient record for the various systems.

Patient data may be used to pre-register a patient prior to arrival for healthcare service. In an emergent situation, such as when a patient may be transported by ambulance to an emergency room, the pre-registration may eliminate precious minutes between when the ambulance arrives at the hospital and when the patient is treated. In a non-emergent situation, such as when a patient schedules an appointment with a healthcare provider ahead of time, the patient may skip filling out various forms and collecting data prior to being seen by the provider. In some cases, the patient information may include data about the patient's condition, requested treatments, or other information that a healthcare provider may use to prepare the facilities or treatment plan. Patient pre-registration may dramatically increase the accuracy and speed of handling patient records.

Patient data may be sent to a hospital accounting system 124. Such information may start a billing record for the patient's visit to the healthcare provider. The billing record may be populated later by a healthcare provider. In many cases, a patient records system may provide a healthcare provider with a pre-populated billing record for the healthcare provider to fill out.

A transportation agency system 126 may receive patient information for billing and accounting uses. A transportation agency may be a fire department, ambulance service, nursing home, or other agency that may transport the patient to a healthcare facility. Typically, such agencies either bill for service or at least track activities performed by the agency. By having the patient information automatically sent to the transportation agency system 126, paperwork and administrative overhead may be reduced, and the accuracy of the information may be improved over manual systems.

Some systems may permit a return message 120 to be generated by a receiving device, such as a hospital registration computer system 116, where the return message 120 may be transmitted to the remote service 114 and forwarded as a return message 122 to the mobile telephone 110. Although not illustrated, the other various systems may also create return messages that may be passed to the original device used to capture the patient information, including the hospital accounting system 124, transportation agency system 126, patient records system 128, or other systems that may receive the patient information.

The return message 122 may be a simple acknowledgement of receipt, may request additional information, may request verification of the patient information, or may contain other information for either the patient or the person who may be assisting the patient.

Figure 2:
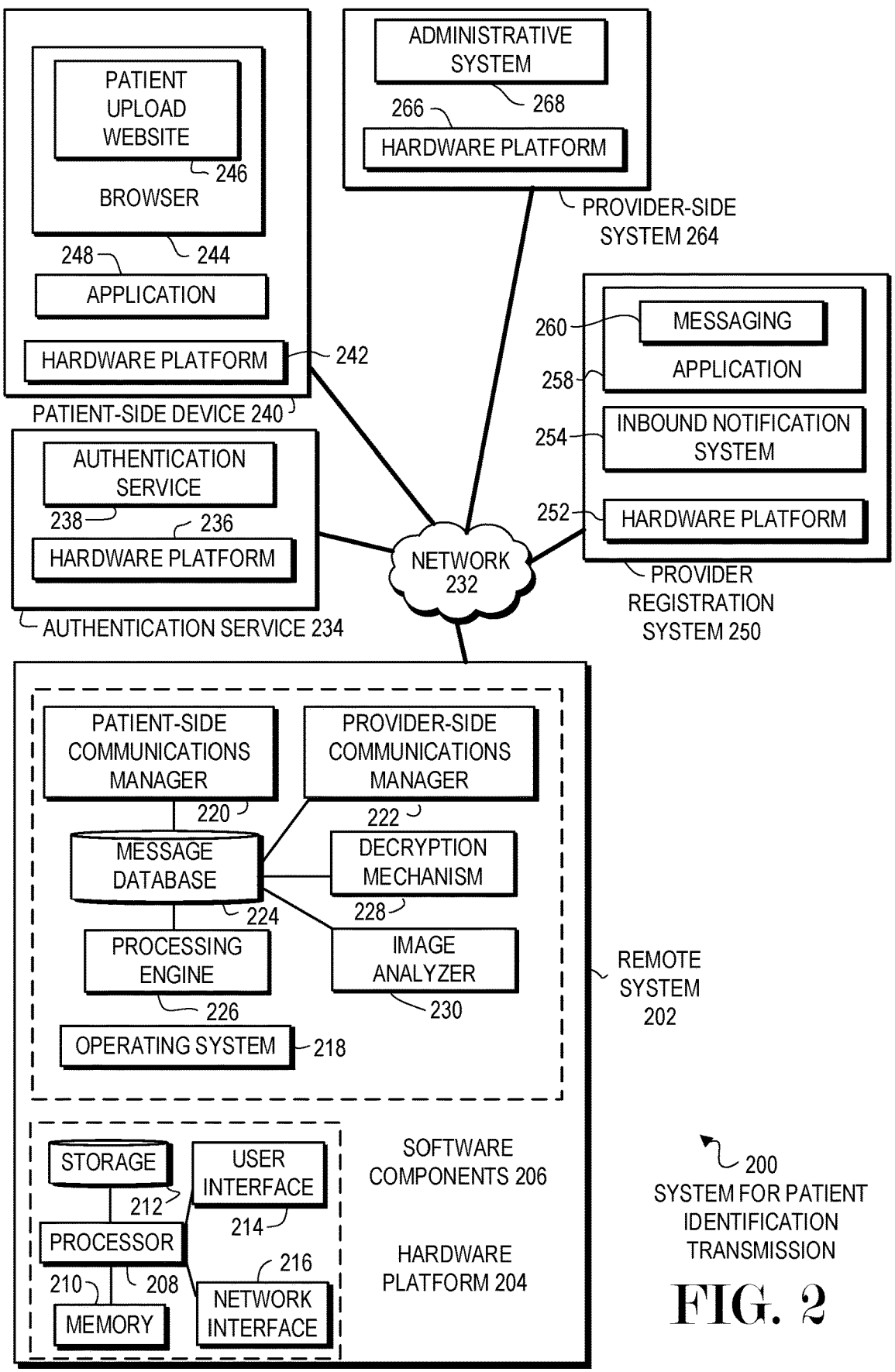
FIG. 2 is a diagram illustration of an embodiment showing a network environment showing a system for patient identification.

FIG. 2 is a diagram of an embodiment 200 showing components that may communicate from a patient-side device to provider-side systems through a remote service. Embodiment 200 is merely one architecture that may illustrate various components that may interact to provide communications between patients or first responders and other healthcare service providers. Other embodiments may have different architectures.

The diagram of FIG. 2 illustrates functional components of a system. In some cases, the component may be a hardware component, a software component, or a combination of hardware and software. Some of the components may be application level software, while other components may be execution environment level components. In some cases, the connection of one component to another may be a close connection where two or more components are operating on a single hardware platform. In other cases, the connections may be made over network connections spanning long distances. Each embodiment may use different hardware, software, and interconnection architectures to achieve the functions described.

Embodiment 200 illustrates a device 202 that may have a hardware platform 204 and various software components. The device 202 as illustrated represents a conventional computing device, although other embodiments may have different configurations, architectures, or components.

In many embodiments, the device 202 may be a server computer. In some embodiments, the device 202 may still also be a desktop computer, laptop computer, netbook computer, tablet or slate computer, wireless handset, cellular telephone, game console or any other type of computing device. In some embodiments, the device 202 may be implemented on a cluster of computing devices, which may be a group of physical or virtual machines.

The hardware platform 204 may include a processor 208, random access memory 210, and nonvolatile storage 212. The hardware platform 204 may also include a user interface 214 and network interface 216.

The random access memory 210 may be storage that contains data objects and executable code that can be quickly accessed by the processors 208. In many embodiments, the random access memory 210 may have a high-speed bus connecting the memory 210 to the processors 208.

The nonvolatile storage 212 may be storage that persists after the device 202 is shut down. The nonvolatile storage 212 may be any type of storage device, including hard disk, solid state memory devices, magnetic tape, optical storage, or other type of storage. The nonvolatile storage 212 may be read only or read/write capable. In some embodiments, the nonvolatile storage 212 may be cloud based, network storage, or other storage that may be accessed over a network connection.

The user interface 214 may be any type of hardware capable of displaying output and receiving input from a user. In many cases, the output display may be a graphical display monitor, although output devices may include lights and other visual output, audio output, kinetic actuator output, as well as other output devices. Conventional input devices may include keyboards and pointing devices such as a mouse, stylus, trackball, or other pointing device. Other input devices may include various sensors, including biometric input devices, audio and video input devices, and other sensors.

The network interface 216 may be any type of connection to another computer. In many embodiments, the network interface 216 may be a wired Ethernet connection. Other embodiments may include wired or wireless connections over various communication protocols.

The software components 206 may include an operating system 218 on which various software components and services may operate.

The remote service 202 may have a patient-side communications manager 220 and a provider-side communications manager 222. The patient-side communications manager 220 may handle all communication with devices that may generate patient information, such as the mobile telephone 110 illustrated in embodiment 100. The provider-side communications manager 222 may communicate with various healthcare provider systems, such as patient record systems, registration and scheduling systems, accounting and bill collection systems, and other systems.

A message database 224 may contain the messages handled by the remote service 202. In some systems, the messages in the message database may be encrypted messages that may have been encrypted by the sending device and may not have been decrypted by the remote service 202. In other systems, the message database 224 may contain decrypted messages that may be processed in various forms.

A provider-side processing engine 226 may process incoming messages from patient-side devices and perform various functions. For example, a decryption mechanism 228 may decrypt an incoming message and an identification image analyzer 230 may perform optical character recognition of an image of a patient's driver's license, insurance card, or other identification. The processing engine 226 may populate various database fields with data gathered from the optical character recognition process, and may perform other tasks in conjunction with other systems.

An authentication service 234 may be used by various components to authenticate services, devices, users, and other elements. The authentication service 234 may have a hardware platform 236 on which an authentication system 238 may operate. The authentication system 238 may receive credentials and may return an authentication token.

A patient-side device 240 may be a mechanism by which emergency personnel or other third parties may be able to upload patient identification. In some use cases, the patient may upload their identification themselves, such as when scheduling an appointment with a healthcare provider.

One implementation may have a browser 244 in which a patient upload website 246 may operate. In such an implementation, the website may provide various mechanisms for uploading patient information to the remote service 202. Such mechanisms may include secure connections, input mechanisms for images, as well as text, video, audio, or other information.

Another implementation may have an application 248 which may execute on the hardware platform 242. The application 248 may perform the tasks of data collection and uploading, and may use native calls or other features of the hardware platform 242 that may not be accessible through a browser 244. In one example, an application 248 may be able to access a device's camera while bypassing or disabling local storage and screen capture of the device, where local storage and screen capture may not be able to be disabled using a browser.

A provider registration system 250 may be a system that may be used to help check in a patient upon arrival. A hardware platform 252 may have an inbound notification system 256, as well as an application for displaying patient information 258. The application for displaying patient information 258 may have a messaging system 260 as well as a connection to other provider systems.

An example of a provider-side systems 264 may have a hardware platform 266 and an administrative system 268. The administrative system 268 may be a patient monitoring application, patient billing application, insurance reporting application, patient records application, transport agency application, or any other application. In many cases, the processing engine 226 may create a message for a provider administrative system 268 that contains a subset or superset of data that may have been extracted from a patient identification message. A subset may be useful when an application may use only a portion of the patient information and the provider administrative system 268 may not have permission for accessing any additional data. A superset may be useful when the processing engine 226 may gather additional data from various systems, such as a patient's records, and create a message that may contain data from the patient identification message as well as other sources of data.

The processing engine 226 and message database 224 may provide an audit trail for communications regarding a patient. The audit trail may be used for compliance or insurance audits, such as for determining whether certain services were appropriate and whether such services were actually provided. The audit train may be useful for financial audits, to determine whether proper payments were made for services that were actually rendered.

Figure 3:
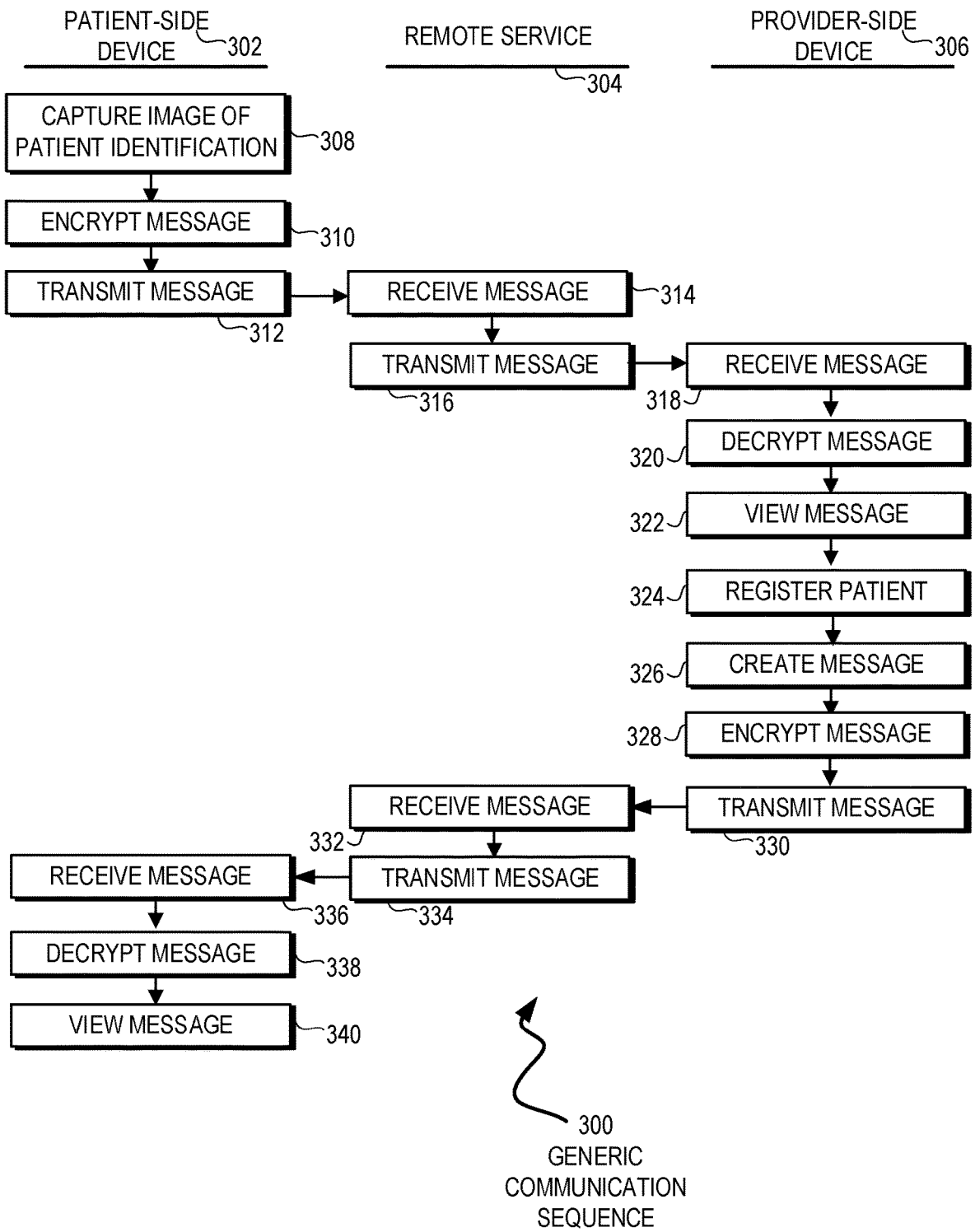
FIG. 3 is a flowchart diagram of an embodiment showing a method for a generic communication system.

FIG. 3 is a flowchart illustration of an embodiment 300 showing a simplified example of operations between a patient-side service 302, a remote service 304, and a provider-side service 306. The operations of the patient-side service 302 are illustrated in the left hand column, the operations of the remote service 304 are illustrated in the center column, and the operations of the provider-side service 306 are illustrated in the right hand column.

Other embodiments may use different sequencing, additional or fewer steps, and different nomenclature or terminology to accomplish similar functions. In some embodiments, various operations or set of operations may be performed in parallel with other operations, either in a synchronous or asynchronous manner. The steps selected here were chosen to illustrate some principles of operations in a simplified form.

Embodiment 300 is merely one simplified illustration of the interactions between the various devices. This illustration may leave out several steps, some of which are disclosed in detail in subsequent figures.

The patient-side device 302 may be any device where patient information may originate and be sent to a healthcare provider. One of the examples used in this specification may be a device operated by a paramedic on an ambulance crew, who may take a picture of a patient's driver's license and send the image ahead to the hospital. The hospital may receive the image and have the patient pre-registered when the patient arrives.

Another example may be a patient who may use a website or application to upload their data as part of scheduling an appointment. Such a use cases may be an emergent or non-emergent situation.

A provider-side device 306 may be any device used by a healthcare professional. In some cases, the healthcare professional may be a doctor, nurse, or other direct care provider, while in other cases, the healthcare professional may be an administrative clerk or other non-direct care staff.

The patient-side device 302 may capture an image of a patient identification in block 308. The image may be taken with the device's camera or with another device that may capture the image. The image may be encrypted into a message in block 310 and may be transmitted in block 312 to the remote service 304, which may receive the message in block 314.

The remote service 304 may transmit the message in block 316 to the provider-side device 306, which may receive the message in block 318. In some cases, the remote service 304 may transmit the message in its original encrypted form, while in other cases, the remote service 304 may decrypt the message. In some such cases, the remote service 304 may process the message in various manners prior to transmitting the message.

The provider-side device 306 may decrypt the message in block 320, may view the message in block 322, and may register the patient in block 324. In one implementation of the system, the provider-side device 306 may be a handheld or tablet computer, which may be at a nurse's station in an emergency department. An incoming message may include an image of an inbound patient's driver's license, and the hospital staff may be able to enter the patient's information into the hospital's registration system and otherwise prepare to receive the patient.

Some systems may allow a user of the provider-side device 306 to create a message in block 326, encrypt the message in block 328, and transmit the message in block 330 to the remote service 304. The remote service 304 may receive the message in block 332, then transmit the message in block 334 to the patient-side device 302. The patient-side device 302 may receive the message in block 336, decrypt the message in block 338, and view the message in block 340.

One use case of the return message may be to acknowledge receipt of the original message. Another use case may be to ask for clarifying information, such as when the image of a patient's driver's license may not be clear or is out of focus. Still another use case may be to direct an ambulance or patient to a different location for healthcare. For example, a patient with a specific insurance policy or health plan may be routed to a hospital or provider in their network, rather than to a more expensive alternative. In some cases, a patient's specific ailment may cause the patient to be routed to a facility better able to treat the ailment.

Figure 4:
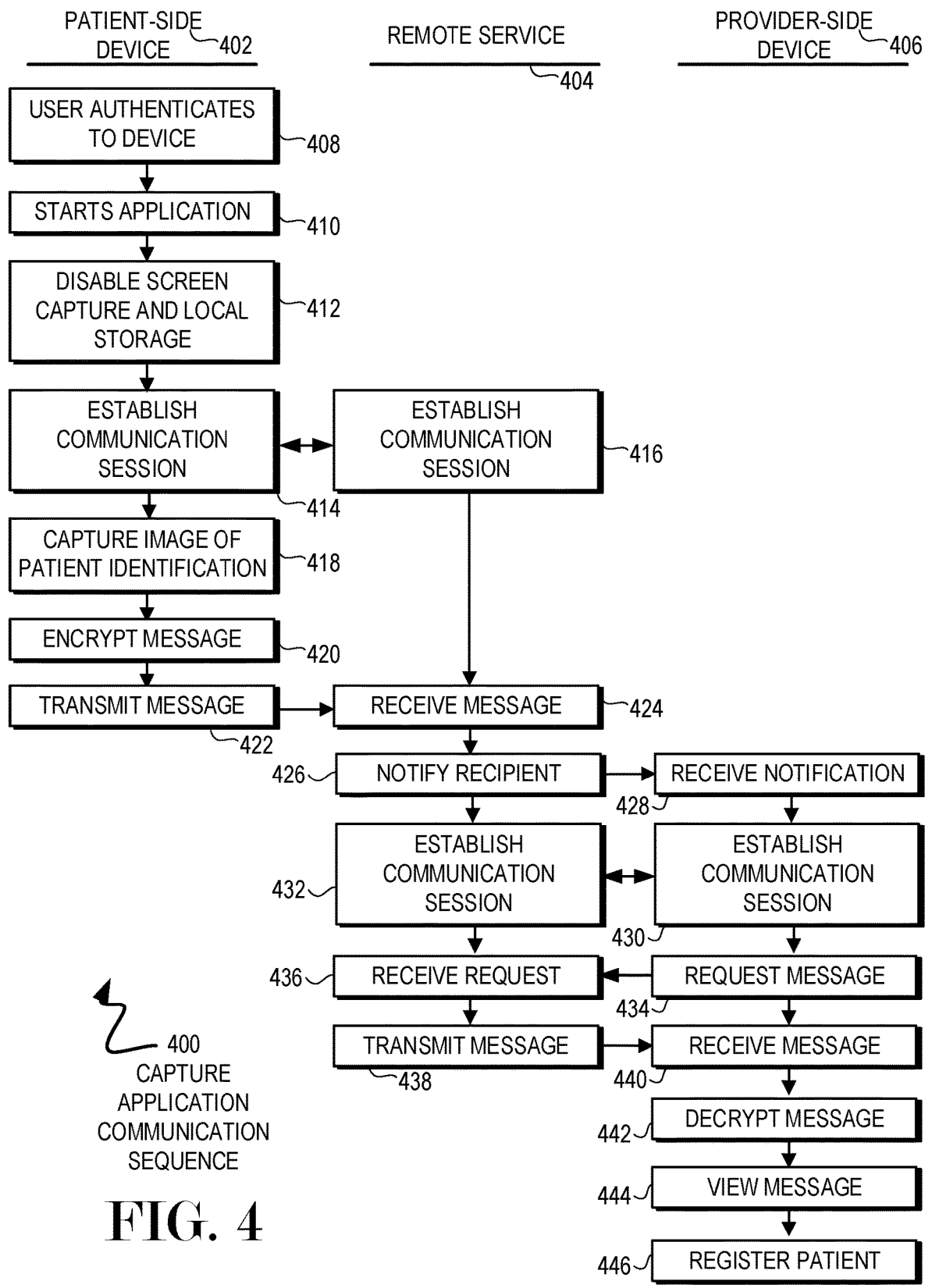
FIG. 4 is a flowchart diagram of an embodiment showing a method for an application based communication system.

FIG. 4 is a flowchart illustration of an embodiment 400 showing a second example of operations between a patient-side service 402, a remote service 404, and a provider-side service 406. The operations of the patient-side service 402 are illustrated in the left hand column, the operations of the remote service 404 are illustrated in the center column, and the operations of the provider-side service 406 are illustrated in the right hand column.

Other embodiments may use different sequencing, additional or fewer steps, and different nomenclature or terminology to accomplish similar functions. In some embodiments, various operations or set of operations may be performed in parallel with other operations, either in a synchronous or asynchronous manner. The steps selected here were chosen to illustrate some principles of operations in a simplified form.

Embodiment 400 is merely another simplified illustration of the interactions between the various devices. This illustration shows a use case that may happen with a device that may be configured with an application that may capture and encrypt patient information, and a remote service that may notify a provider-side device prior to transmitting a massage with patient information. The notification may alert a person at a hospital or other healthcare facility that a patient may be inbound, and provider-side device may request the message when ready to receive it.

The patient-side device 402 may begin when a user authenticates to the device in block 408. The user may start the application in block 410, and the application may disable screen capture and local storage or make other configuration changes in block 412.

The application may configure the device for secure operations by disabling various functions. In this example, screen capture and local storage are two examples of typical functions found on a portable device, and such functions may pose a security weakness. Other devices may have other functions that may be disabled or enabled prior to operating the application. In some cases, the device may have security features that may be enabled prior to executing the application.

A communication session may be established in blocks 414 and 416 between the patient-side device 402 and the remote service 404. Such a communication session may or may not be an authenticated session where user or device credentials may be used for authentication. The communication session of blocks 414 and 416 may be a secure communication session, where the communications are encrypted.

An image of a patient's identification may be captured in block 418, then encrypted in block 420 and transmitted in block 422. In some cases, the encryption of block 420 may be an explicit encryption step where an encrypted version of the image may be created prior to creating a message to transmit. In other cases, such as when the communication session is an encrypted or secure session, the patient identification may be encrypted by virtue of the secure communications session. In such a case, the encryption may be an artifact of the secure communications session and may not be a separate step performed prior to transmission.

The remote service 404 may receive the message in block 424 and may transmit a notification in block 426. The provider-side device 406 may receive the notification in block 428 and may establish a communication session in blocks 430 and 432 with the remote service 404. After the session may be established, the provider-side device 406 may request the message in block 434.

The request may be received in block 436 by the remote service 404, which may transmit the message in block 438. The provider-side device 406 may receive the message in block 440, decrypt the message in block 442, view the message in block 444, and register the patient in block 446.

The sequence of notifying the provider-side device in block 426 prior to establishing a communication session in blocks 430 and 432 may be useful when authentication may be used to establish the communication session. Such a sequence may allow an unsecure notification message to be sent to the provider-side device 406, then after a user authenticates to the remote service 404, the communication session of blocks 430 and 432 may be established.

Figure 5:
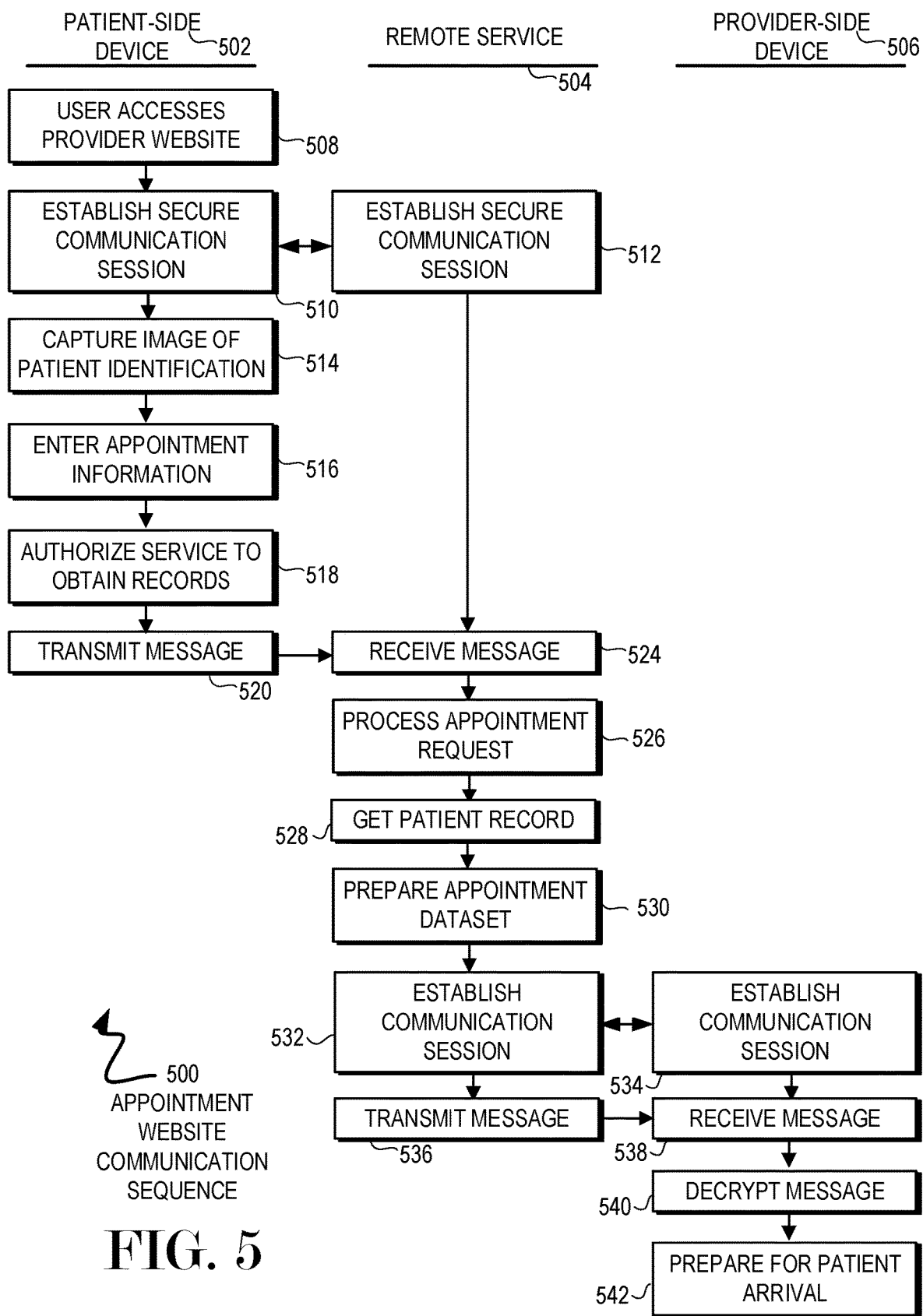
FIG. 5 is a flowchart diagram of an embodiment showing a method for an appointment website communication system.

FIG. 5 is a flowchart illustration of an embodiment 500 showing a third example of operations between a patient-side service 502, a remote service 504, and a provider-side service 506. The operations of the patient-side service 502 are illustrated in the left hand column, the operations of the remote service 504 are illustrated in the center column, and the operations of the provider-side service 506 are illustrated in the right hand column.

Other embodiments may use different sequencing, additional or fewer steps, and different nomenclature or terminology to accomplish similar functions. In some embodiments, various operations or set of operations may be performed in parallel with other operations, either in a synchronous or asynchronous manner. The steps selected here were chosen to illustrate some principles of operations in a simplified form.

Embodiment 500 is yet another simplified illustration of the interactions between the various devices. This illustration may show a user interaction between a patient-side device 502 and a remote service 504 using a website interface. A typical use case may be for a patient or a caregiver to schedule an appointment with a healthcare provider.

On a patient-side device 502, a user may access a provider website in block 508, which may be hosted by the remote service 504. The website session may be a secure communication session in blocks 510 and 512.

With the communication session open, an image may be captured of the patient's identification in block 514. Various appointment related information may be entered in block 516, and an authorization may be made in block 518 to obtain the patient's records for the requested appointment. A message may be transmitted in block 520, which may be received by the remote service 505 in block 524.

In some cases, the information transmitted by one message may be transmitted in a series of messages, and the series of messages may be sent in response to various steps of input by a user. For simplicity, such multiple messages may be represented by the single message of block 520 and other similar representations throughout this specification.

The remote service 504 may process the appointment request in block 526, the patient's records may be retrieved in block 528, and an appointment dataset may be prepared in block 530. The appointment dataset may include as much information as may be available for the requested treatment. In many cases, such information may be formatted and verified for use with a provider's administrative systems, such as a scheduling system, patient record system, or other systems.

A communication session may be established in blocks 532 and 534. A message may be transmitted in block 536 and received in block 538 by the provider-side device 506, which may decrypt the message in block 540 and prepare for patient arrival in block 542.

Figure 6:
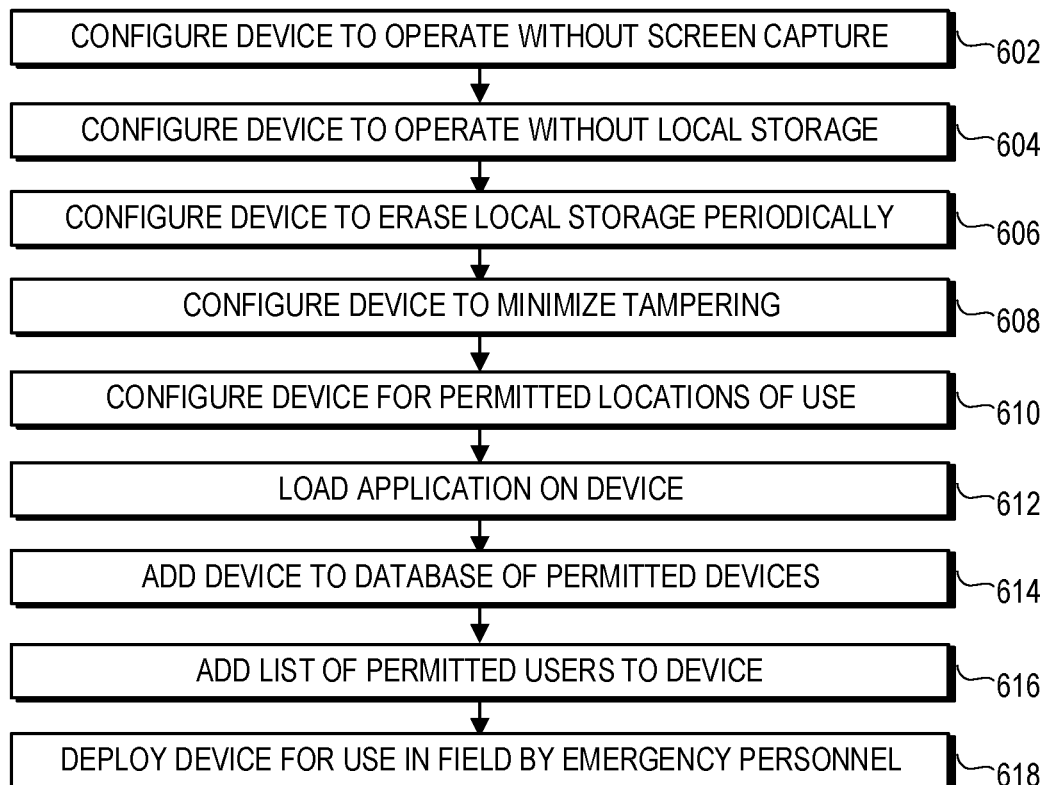
FIG. 6 is a flowchart diagram of an embodiment showing a method for configuring a device for use in the field.

FIG. 6 is a flowchart illustration of an embodiment 600 showing a simplified example of operations that may be performed to prepare a device for use in the field.

Other embodiments may use different sequencing, additional or fewer steps, and different nomenclature or terminology to accomplish similar functions. In some embodiments, various operations or set of operations may be performed in parallel with other operations, either in a synchronous or asynchronous manner. The steps selected here were chosen to illustrate some principles of operations in a simplified form.

Embodiment 600 is merely one simplified illustration of operations that may be performed to configure a patient-side device for use in the field. This example may be for a device used by emergency personnel who may be transporting patients to a healthcare provider, such as paramedics who may be transporting patients to a hospital.

The device may be configured to operate without a screen capture function in block 602, and operate without local storage in block 604. In cases where a device may not have local storage completely disabled, the device may be configured in block 606 to erase local storage periodically.

Various other configuration changes may be made in block 608 to minimize tampering. Such changes may include configuring the device for specific users, defining specific password complexities, specifying biometric or other authentication parameters, or other changes as may apply to various devices.

In some cases, the device may be configured to operate in specific geographical areas in block 610. Such a configuration may allow the device to operate within a specific boundary, but may disable or have reduced capabilities when the device is brought outside the boundary. For example, an ambulance service may be licensed and may operate in a specific city or state, and when their devices may be brought outside of that boundary, they devices may disable themselves. In some cases, such devices may automatically erase certain data, go into an emergency mode, or perform some other function.

An application may be loaded on the device in block 612. The application may be a customized application that may establish secure communications with a remote service, provide encryption, authentication, and various other operations.

The device may be added to a database of permitted devices in block 614, and a list of permitted users may be added in block 616. Such operations may be performed with an authentication system that may be part of or accessed by a remote service.

Once configured, the device may be deployed in the field for use by emergency personnel in block 618.

Figure 7:
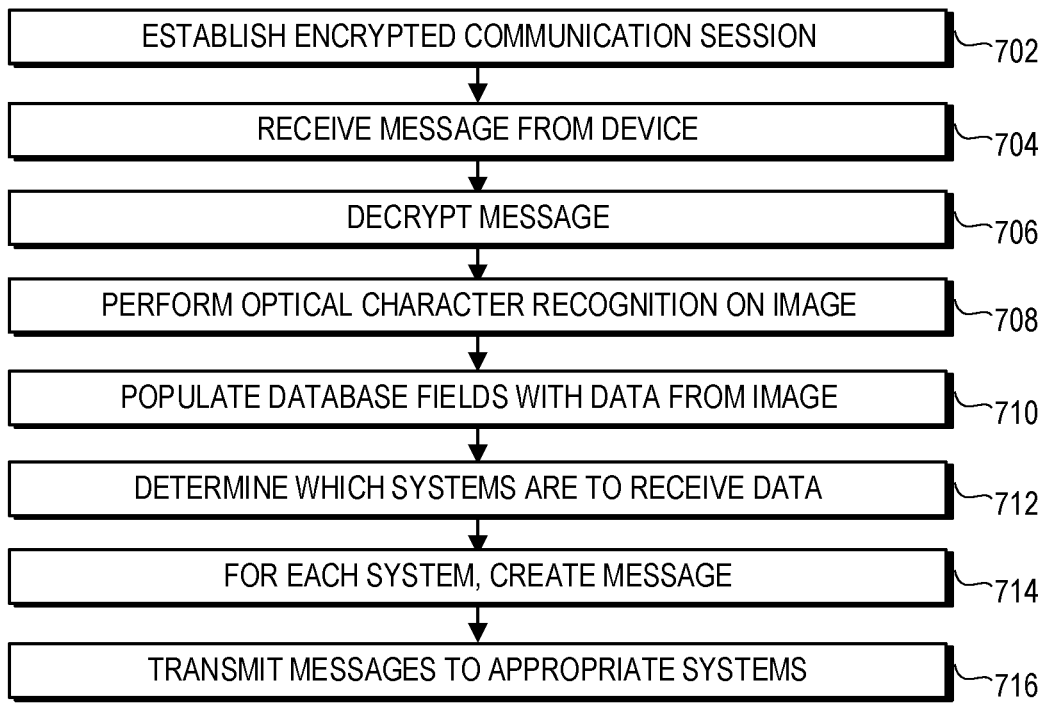
FIG. 7 is a flowchart diagram of an embodiment showing a method for remote service activities.

FIG. 7 is a flowchart illustration of an embodiment 700 showing a simplified example of operations that may be performed by a remote service.

Other embodiments may use different sequencing, additional or fewer steps, and different nomenclature or terminology to accomplish similar functions. In some embodiments, various operations or set of operations may be performed in parallel with other operations, either in a synchronous or asynchronous manner. The steps selected here were chosen to illustrate some principles of operations in a simplified form.

Embodiment 700 is merely one simplified illustration of operations that may be performed by a remote service when receiving a message from a patient-side device.

An encrypted communication session may be established in block 702 with a patient-side device, through which a message may be received in block 704. The message may be decrypted in block 706.

Within a message may be an image of a patient identification document, such as an insurance card, driver's license, employment identification, passport, government issued identification, social security card, or any other identification document.

An optical character recognition operation may be performed on the image in block 708. An analysis of the document may identify various database fields that may be populated from the image in block 710. Such fields may be the patient's name, address, social security number, driver's license number, age, height, weight, insurance carrier, insurance plan, minimum copay, or any other field that may be extracted from the document.

The provider-side systems that may receive data may be identified in block 712. For each of the designated systems, a message may be created in block 714 and transmitted in block 716.

The foregoing description of the subject matter has been presented for purposes of illustration and description. It is not intended to be exhaustive or to limit the subject matter to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments except insofar as limited by the prior art.

The invention claimed is:

1. A system comprising:
at least one processor;
a display screen;
a local non-volatile storage;
a communications interface;
an application:
    capturing patient information;
    displaying at least a portion of said patient information;
    encrypting said patient information to create encrypted patient information; and
    transmitting said encrypted patient information over said communications interface;
said application further disabling said local non-volatile storage during at least said displaying said at least a portion of said patient information.

2. The system of claim 1 further comprising:
a camera capable of capturing a camera image;
said application further:
    capturing patient image information using said camera; and
    disabling storage of said patient image information to said local non-volatile storage.

3. The system of claim 2 further comprising:
said camera further capable of storing said camera image in said local non-volatile storage when said application has not disabled said storage of said patient image information.

4. The system of claim 3 further comprising:
an image manipulation function;
said application further disabling said image manipulation function during at least said displaying said at least a portion of said patient information.

5. The system of claim 1, said application further receiving user authentication prior to operation.

6. The system of claim 5, said user authentication being received from a first person, said patient information referring to a second person.

7. The system of claim 1 further comprising:
a location determination mechanism;
said application:
    determining a physical location for said system from said location determination system;
    determining said physical location is outside a predetermined boundary; and
    not permitting said application to operate further when said physical location is outside said predetermined boundary.

8. The system of claim 1 said application:
receiving a message from a remote location; and
displaying at least a portion of said message on said display screen.

9. The system of claim 8, said message being received in encrypted form and being displayed in an unencrypted form.

* * * * *